(12) United States Patent
Binkley et al.

(10) Patent No.: US 7,963,163 B2
(45) Date of Patent: Jun. 21, 2011

(54) SYSTEMS AND METHODS FOR DETECTING FLUIDS

(75) Inventors: John E. Binkley, Jacksonville, FL (US); Shane E. Myers, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1645 days.

(21) Appl. No.: 11/250,732

(22) Filed: Oct. 14, 2005

(65) Prior Publication Data

US 2007/0084287 A1 Apr. 19, 2007

(51) Int. Cl.
*G01F 23/296* (2006.01)
(52) U.S. Cl. .......................................... 73/290 V
(58) Field of Classification Search .................. 73/290 V
See application file for complete search history.

(56) References Cited

U.S. PATENT DOCUMENTS

| | | | |
|---|---|---|---|
| 4,883,100 A * | 11/1989 | Stembridge et al. | 141/1 |
| 4,984,449 A | 1/1991 | Caldwell et al. | |
| 5,121,628 A * | 6/1992 | Merkl et al. | 73/290 V |
| 5,578,331 A | 11/1996 | Martin et al. | 425/445 |
| 5,623,816 A * | 4/1997 | Edwards et al. | 53/478 |
| 2004/0112008 A1 | 6/2004 | Voss et al. | 53/329.3 |

FOREIGN PATENT DOCUMENTS

| | | |
|---|---|---|
| EP | 0393687 | 10/1990 |
| FR | 2328951 | 5/1977 |
| FR | 2328951 A * | 6/1977 |
| WO | WO 98/32587 | 7/1998 |

OTHER PUBLICATIONS

HydePark® Sensors for the Real World, Ultrasonic Sensors, Catalog vol. 105, a company of Schneider Electric, Copyright 2004, Hyde Park Electronics LLC, i-ii-7-6.
PCT International Search Report, dated Jan. 1, 2007, for PCT Int'l. Appln. No. PCT/US2006/039849.

* cited by examiner

*Primary Examiner* — Hezron Williams
*Assistant Examiner* — Rose M Miller

(57) ABSTRACT

Fluids such as saline solution that are disposed in containers such as contact lens packages can be detected by directing ultrasonic energy at the container and receiving a return reflection of the ultrasonic energy. The ultrasonic energy and the return reflection can propagate through a shroud that substantially isolates the ultrasonic energy and the return reflection from air currents.

5 Claims, 9 Drawing Sheets

SYSTEMS AND METHODS FOR DETECTING FLUIDS

FIELD OF THE INVENTION

The present invention relates to systems and methods for determining whether a fluid, such as saline solution, is present in a container, such as a package for storing a contact lens.

BACKGROUND OF THE INVENTION

Contact lenses are commonly provided to the consumer in containers in the form of plastic packages. A typical package includes defines one or more cups each suitable for holding a contact lens. Each cup is usually filled with saline solution that immerses the contact lens, and maintains the contact lens in a hydrated condition. The cup may be covered by a piece of aluminum foil, or other suitable material, applied to the package after the contact lens and saline solution are introduced into the cup. The packaging process is typically performed using automated equipment centrally controlled by a programmable logic controller or other suitable control device.

The cups of the packages may be filled using pumps that deliver a metered dose of saline solution. The centralized control device can be programmed to check whether each pump delivers a dose of saline solution to an associated cup. The controller can perform this function by monitoring whether the pump activates while the cup is positioned to receive saline solution from the pump. A secondary check can be performed before the cup is covered and sealed to verify that saline solution has been delivered to the cup.

The secondary check can be performed using a photoelectric proximity sensor that emits infrared light toward the cup. Saline solution, if present in the cup above a certain level, will reflect the infrared light. The proximity sensor, in turn, can detect the reflected light of a predetermined intensity, as measured by the proximity sensor, can be interpreted as an indication that saline solution is present in the cup above a certain level, e.g., above the half-full mark.

The operation of the sensor is dependent upon alignment of the sensor and the cup. In particular, the infrared beam emitted by the sensor may need to be focused precisely at the apex of the meniscus of the saline solution for the proximity sensor to provide an accurate indication of whether saline solution is present in the cup. The degree of alignment required for the proximity sensor to function optimally may be difficult to achieve and maintain in a production environment.

The operation of the proximity sensor can also be dependent upon the orientation of the meniscus of the saline solution. For example, air bubbles often form in the meniscus during filling of the cup and can alter the orientation of the meniscus, so that the beam of the proximity sensor is no longer focused at the apex of the meniscus. The sensor may issue false readings under such circumstances. In particular, the sensor may falsely indicate that the package does not contain saline solution, leading to an unwarranted rejection of the package and the associated contact lens.

SUMMARY OF THE INVENTION

Fluids such as saline solution that are disposed in containers such as contact lens packages can be detected by directing ultrasonic energy at the container and receiving a return reflection of the ultrasonic energy. The ultrasonic energy and the return reflection can propagate through a shroud that substantially isolates the ultrasonic energy and the return reflection from air currents.

Preferred embodiments of a system comprise a container comprising a surface that forms a cup that holds the saline solution, and an ultrasonic sensor that directs acoustic energy at the surface, and detects a return reflection of the acoustic energy.

Preferred methods comprise directing acoustic energy at a surface of a container, the surface forming a cup that holds saline solution, detecting a return reflection of the acoustic energy, and determining a distance between a point of origin of the acoustic energy and a point of reflection of the acoustic energy based on an elapsed time between directing the acoustic energy at the surface and detecting the reflection of the acoustic energy.

Other preferred embodiments of a system comprise a container having a surface that defines a cup, and a fluid disposed in the cup, an ultrasonic sensor that directs acoustic energy at the surface, detects a return reflection generated by contact between the acoustic energy and the fluid, and generates an output based on an elapsed time between directing the acoustic energy at the surface of the container and detecting the return reflection, and a shroud coupled to the ultrasonic sensor.

Other preferred processes comprise placing a contact lens in a cup of a container, conveying the package to a first position proximate a pump, introducing saline solution into the cup using the pump, determining whether the pump was activated while the package was in the first position, conveying the package to a second position proximate an ultrasonic sensor, and directing acoustic energy at the cup and measuring a reflection of the acoustic energy while the container is in the second position using the ultrasonic sensor.

BRIEF DESCRIPTION OF THE DRAWINGS

The foregoing summary, as well as the following detailed description, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings.

DETAILED DESCRIPTION OF ILLUSTRATIVE EMBODIMENTS

Figure 8:
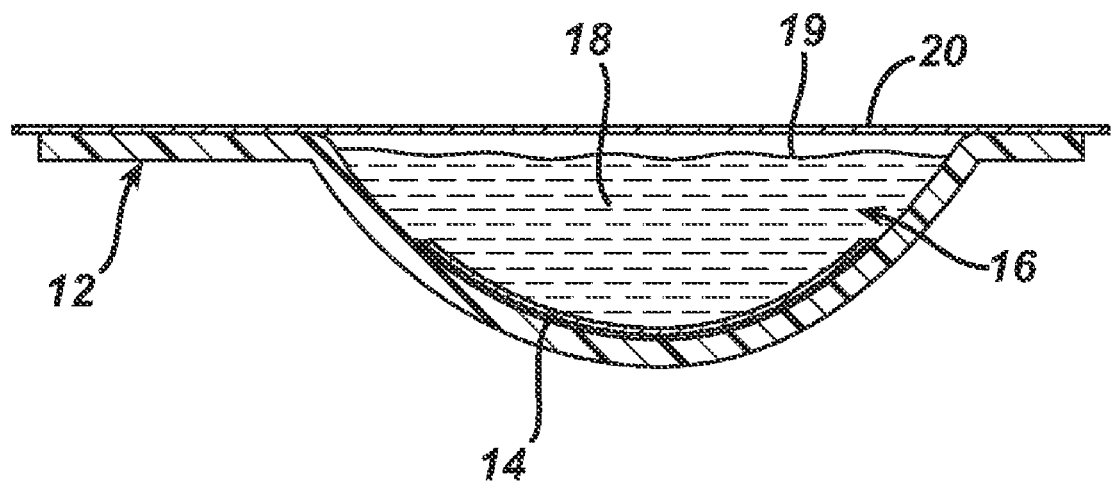
FIG. 8 is a cross-sectional view of a package filled with saline solution and suitable for use with the system shown in FIGS. 1-4.

The figures depict a preferred embodiment of a system 10 for detecting fluid in a container, or package 12. The package 12 can be used to store a contact lens 14 during shipment of the contact lens 14 to the end user. The package 12 defines a semi-spherical bowl, or cup 16, as shown in FIG. 8. The cup 16 holds the contact lens 14. The cup 16 is filled with saline solution 18 that immerses the contact lens 14, and maintains the contact lens 14 in a hydrated condition. The cup 16 can be covered and sealed by a piece of aluminum foil 20 after the contact lens 14 and the saline solution 18 have been introduced into the cup 16. Specific details of the package 12 are disclosed herein for exemplary purposes only. The system 10 can include packages configured differently than the packages 12.

Figure 1:
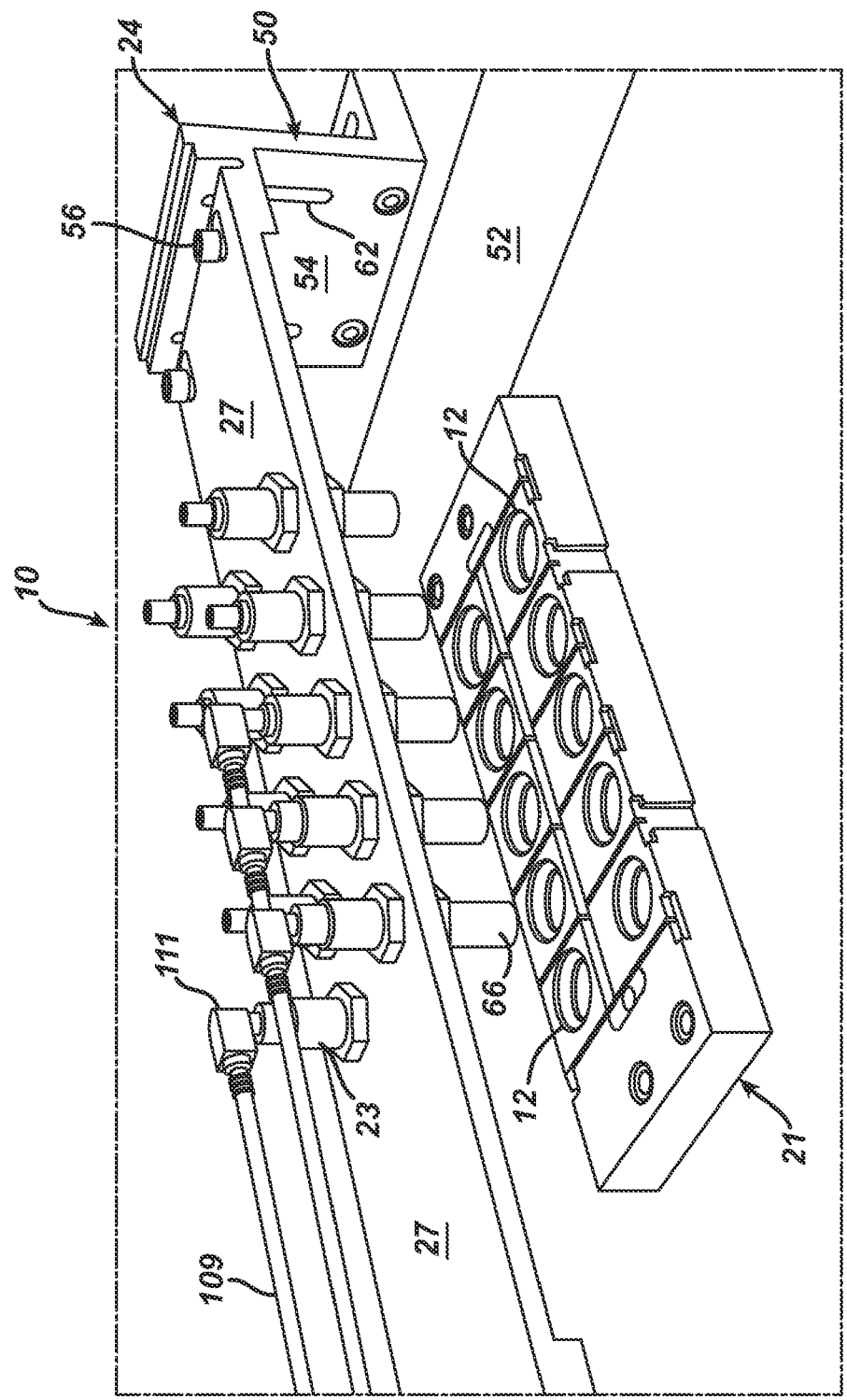
FIG. 1A is a perspective view of a preferred embodiment of a system for detecting fluid in a package.
Figure 2:
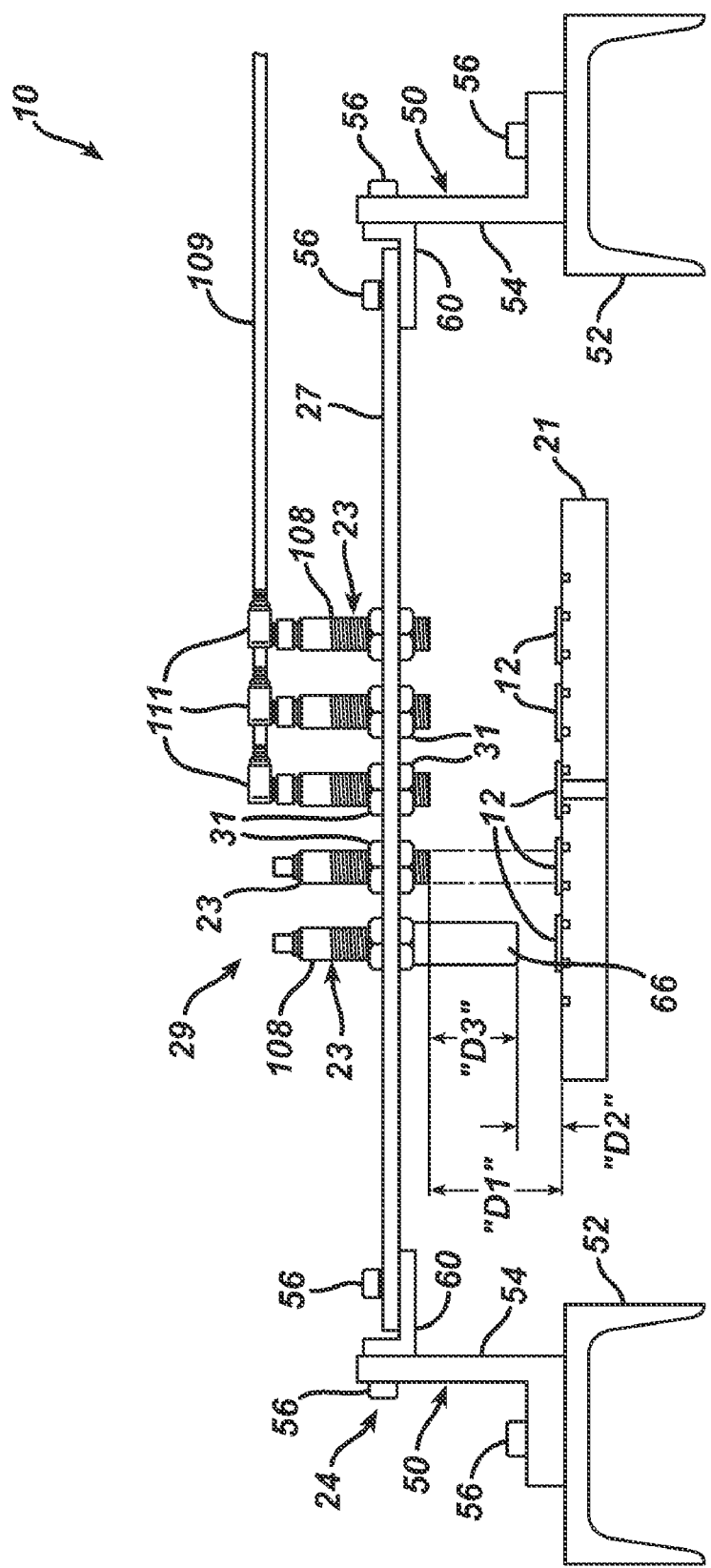
FIG. 2 is a side view of the system shown in FIG. 1.
Figure 9:
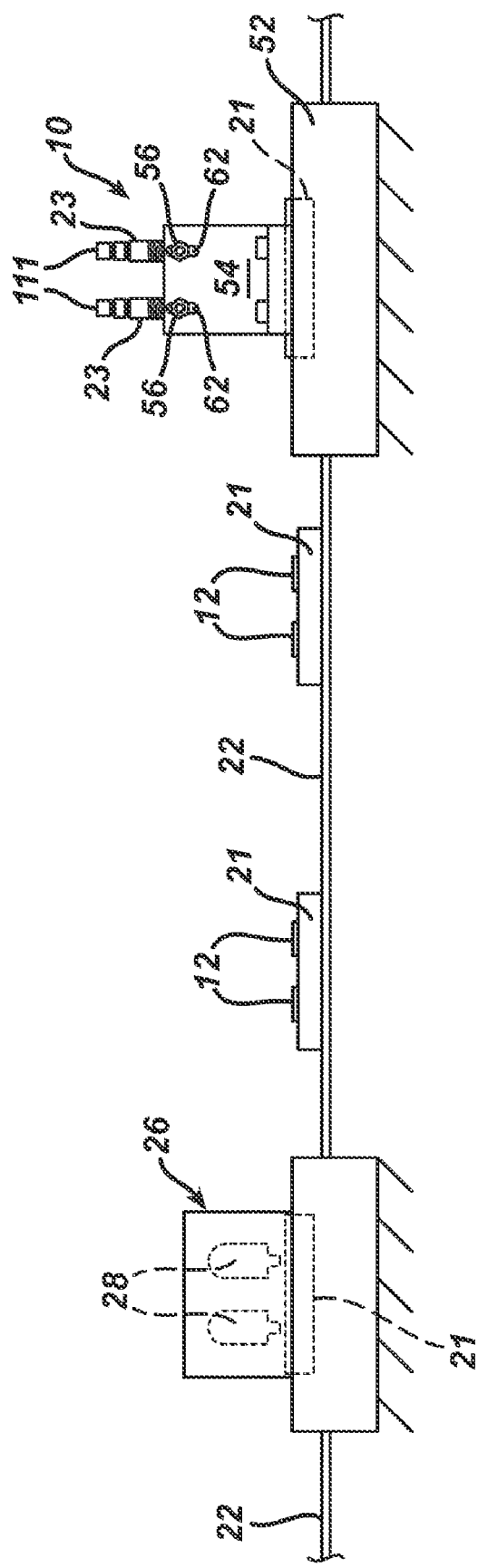
FIG. 9 is a side view of the system shown in FIGS. 1-4, installed as part of a system for packaging contact lenses.

As shown in FIG. 1, the package 12 can be filled with the saline solution 18 at a pump station 26 after the contact lens 14 has been placed in the cup 16. The package 12 can be supported on a pallet 21 as the contact lens 14 and the saline solution 18 are introduced into the cup 16. The pallet 21 is depicted in FIGS. 1, 2, and 9. The pallet 21 can accommodate ten of the packages 12, arranged in two rows of five. The pallet 21 can be transported to and from the pump station 26 by a conveyor 22.

The pump station 26 includes a plurality of pumps 28 for introducing a dose of saline solution 18 into each cup 16 of the packages 12, as shown in FIG. 9. The nominal dose of saline solution 18 fills the cup 16 to within approximately 1.0 mm (0.039 inch) of the upper end of the cup 16.

Figure 10:
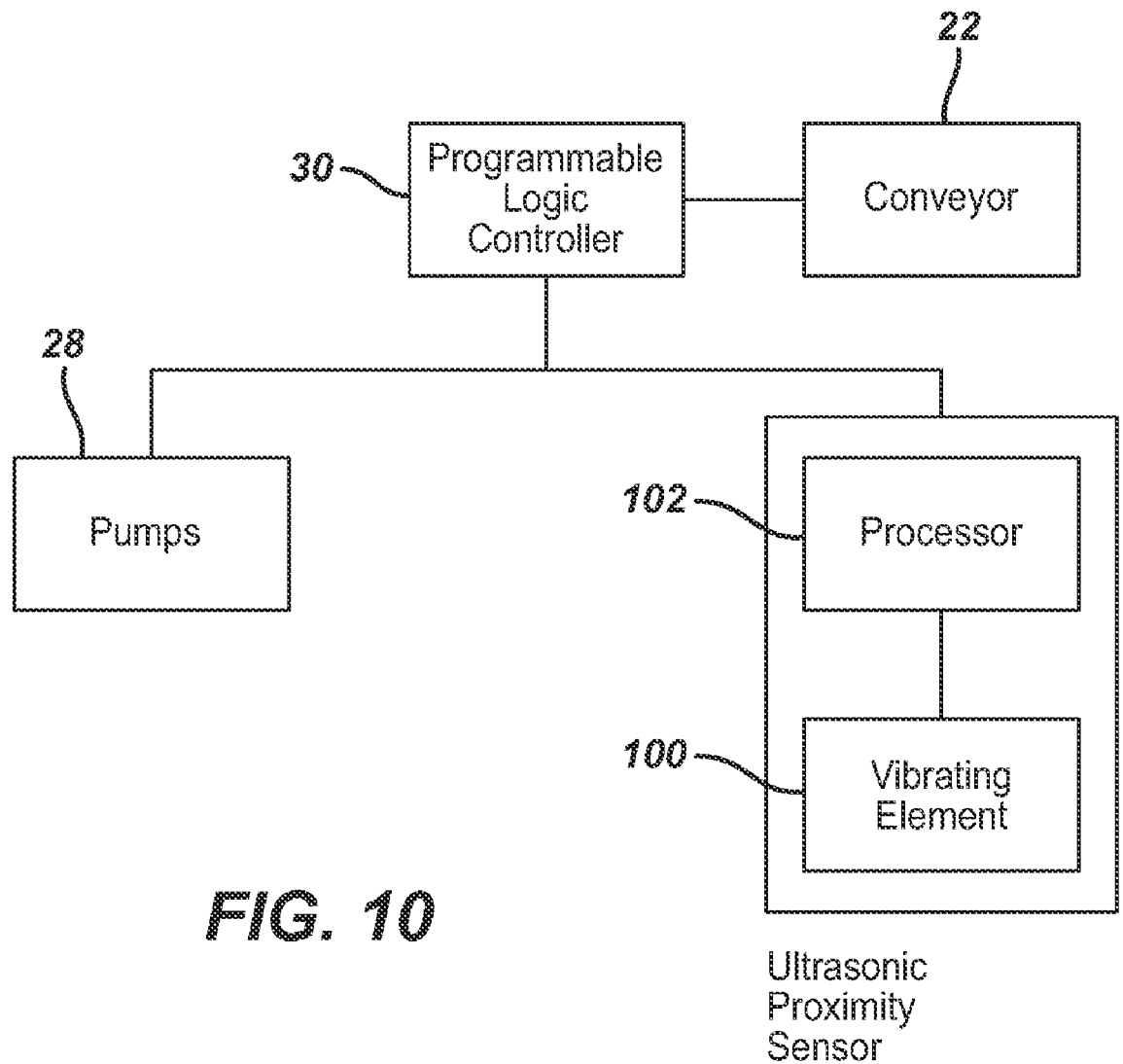
FIG. 10 is a block diagram depicting various components of the system shown in FIG. 9.

As shown in FIG. 10, the pumps 28, conveyor 22, and other equipment associated with the packaging of the contact lenses 14 can be communicatively coupled to a centralized controller, such as a programmable logic controller (PLC) 30. The PLC 30 can coordinate the overall packaging process for the contact lenses 14. The PLC 30 can perform an initial check of whether saline solution 18 has been introduced to each package 12 on the pallet 21 by the pumps 28. In particular, the PLC 30 can be programmed to check whether each pump 28 activates when the pallet 12 is positioned beneath the pump station 26. The PLC 30 can be programmed to classify all of the packages 12 on a particular pallet 21 as rejects if the PLC 30 determines that one or more of the pumps 28 has not activated. The packages 12 designated as rejects can subsequently be disposed of as scrap.

As shown in FIGS. 1-5, the system 10 comprises a plurality of ultrasonic sensors 23, and a mounting structure 24. The sensors 23 can verify that the level of the saline solution 18 in each package 12 is above a predetermined level. The sensors 23 can thereby act as a secondary check that saline solution 18 has been added to each package 12 on a particular pallet 21. If desired, the PLC 30 can be programmed to prevent this check from being conducted on packages 12 designated as rejects during the initial fill check conducted by the PLC 30.

Figure 3:
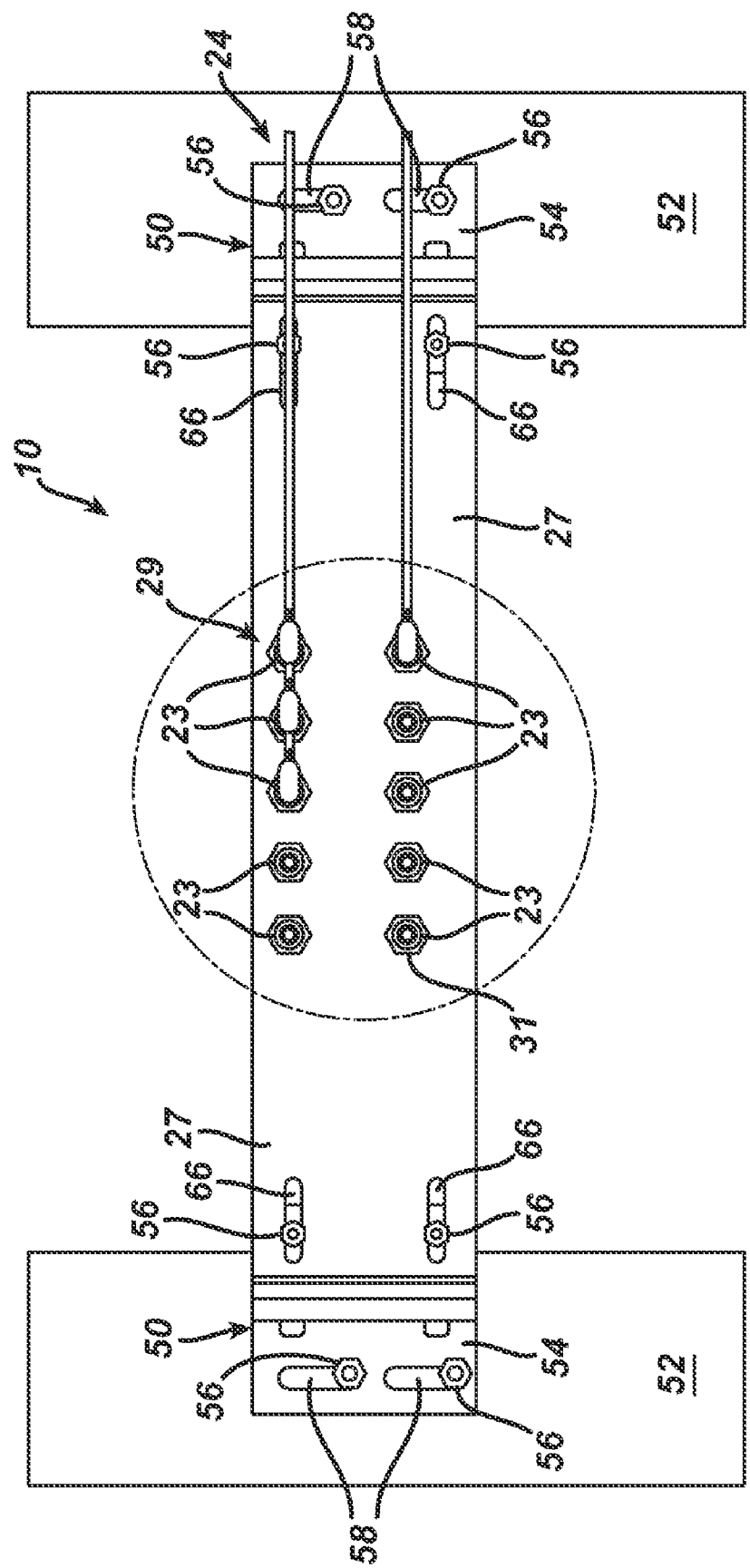
FIG. 3 is a top view of the system shown in FIGS. 1 and 2.
Figure 4:
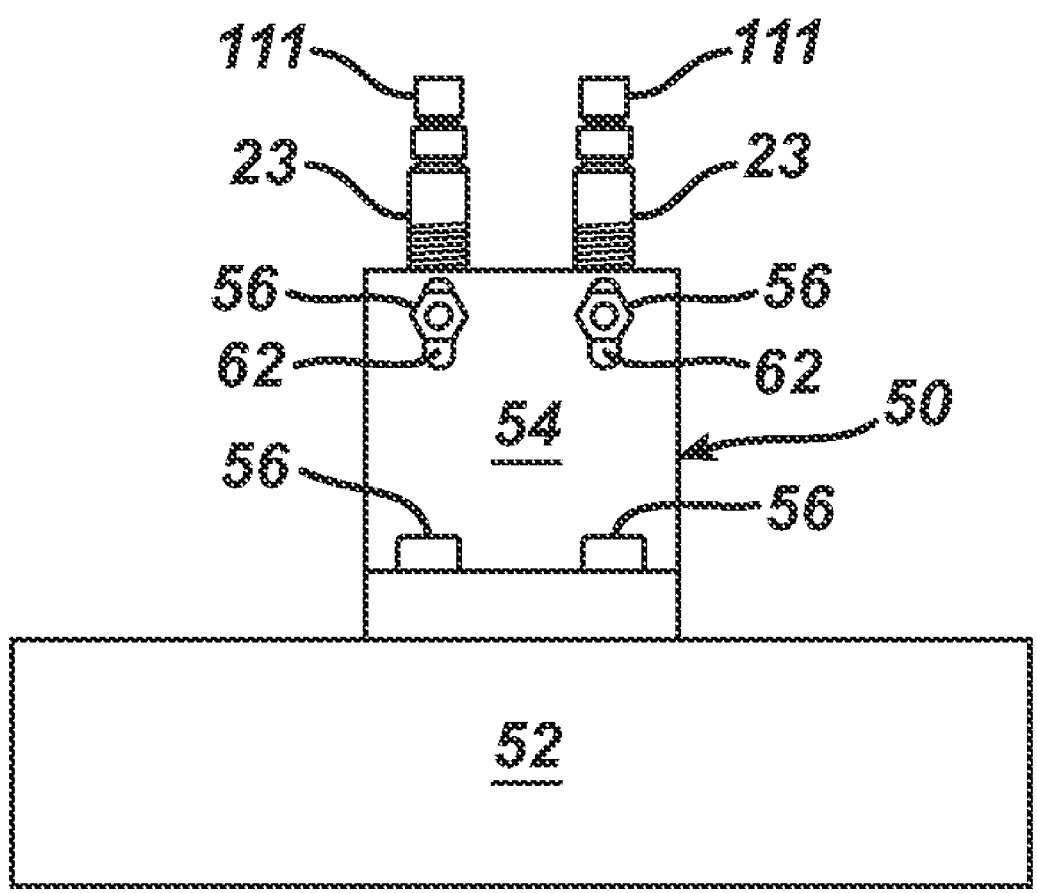
FIG. 4 is a side view of the system shown in FIGS. 1-3, rotated approximately ninety degrees from the perspective of FIG. 2.

As shown in FIGS. 1-3, the sensors 23 are mounted on a plate member 27 of the mounting structure 24. The sensors 23, when mounted on the plate member 27, form an array 29. As in FIGS. 2 and 3, the sensors 23 can be mounted using, for example, nuts 31 having threads that engage complementary threads formed on a housing 108 of associated sensor 23.

The system 10 can include, for example, ten of the sensors 23 arranged in two rows of five, so that the respective levels of saline solution 18 in ten of the packages 12 can be measured simultaneously. The use ten sensors 23 in the array 29 is described for exemplary purposes only. The principles of the present invention can be applied to a single sensor and to sensor arrays having more or less than ten sensors.

The conveyor 22 moves the pallet 21 to a position beneath the array 29 of sensors 23, after the cups 16 have been filled at the pump station 26 (see FIGS. 1 and 9). The sensors 23 are arranged on the plate member 27 so that each sensor 23 can align with an associated package 12 when the pallet 21 is positioned underneath the array 29. In a representative example, the center to center spacing between adjacent sensors 23 in the same row is approximately 30.00 mm (1.181 inches) and the center to center spacing between the two rows can be approximately 50.00 mm (1.969 inches) to substantially match the spacing of the packages 12 on the pallet 21.

The mounting structure 24 supports the bracket member 27 and the array 29 of sensors 23 above the pallet 21. As discussed below, the position of the bracket member 27 can be adjusted in relation to the pallet 21 so that the sensors 23 can be optimally positioned in relation to the corresponding packages 12.

As shown in FIGS. 1-4, the mounting structure 24 preferably includes two bracket assemblies 50, and two base members 52. Each bracket assembly 50 can include a substantially L-shaped lower bracket 54 that is secured to an associated base member 52 by a suitable means such as fasteners 56. The fasteners 56 can be accommodated by slots 58 formed in each lower bracket 54. As shown in FIG. 3, the slots 58 extend in a first direction substantially perpendicular to the lengthwise direction of the plate member 27. This feature permits the positions of the sensors 23 in relation to the pallet 21 (and the packages 12) to be adjusted in the first direction.

The mounting structure 24 further includes two substantially L-shaped upper brackets 60. Each upper bracket 60 is secured to a corresponding lower bracket 54 by a suitable means such as fasteners 56 similar or substantially identical to the fasteners 56 used to secure the lower bracket 54 secured to the base members 52. Each lower bracket 54 has slots 62 formed therein, proximate an upper end thereof, to accommodate these fasteners 56 (see FIGS. 1, 4, and 9). The slots 62 each extend in a second direction coinciding substantially with the vertical direction (from the perspective of FIG. 4). This feature permits the positions of the upper brackets 60 (and the plate member 27 and sensors 23) to be adjusted in relation to the pallet 21 in the second (vertical) direction.

Each upper bracket 60 is secured to a corresponding end of the plate member 27 by a suitable means such as fasteners 56 similar or substantially identical to the fasteners 56 used to secure the lower bracket 54 secured to the base members 52. As shown in FIGS. 1 and 3, the plate member 27 has slots 66 formed therein to accommodate the associated fasteners 56. The slots 66 each extend in a third direction coinciding substantially with the lengthwise direction of the plate member 27. This feature permits the positions of the sensors 23 in relation to the pallet 21 to be adjusted in the third direction.

As shown in FIG. 10, each sensor 23 can include a vibrating element 100, and a processor 102, such as a microprocessor, communicatively coupled to the vibrating element 100. The vibrating element 100 and the processor 102 can be mounted within the housing 108 of the sensor 23. The housing 108 can be, for example, a barrel-type housing. Power and signals can be transmitted to and from the sensors 23 by way of cabling 109 and a connector 111 associated with each sensor 23. (The cabling 109 and connectors 111 associated with several of the sensors 23 are not shown in FIGS. 2 and 3, for clarity.)

The sensor 23 transmits and receives acoustic energy. In particular, the vibrating element 100 of the sensor 23 can generate pulses or bursts of acoustic energy of a predetermined frequency, e.g., 500 kHz. The vibrating element 100 can be, for example, a piezoelectric crystal that vibrates at a predetermined frequency in response to the application of an electric current thereto. The acoustic energy, upon striking an object within the operating distance of the sensor 23, generates a return reflection, or pulse echo. The return reflection, upon reaching the vibrating element 100, causes the vibrating element 100 to vibrate and generate an electrical output.

The processor 102 can be programmed to calculate the presence of an object within the operating distance of the sensor 23. In particular, the processor 102 can be programmed with a time clock that registers the elapsed time between the transmission of the pulse of acoustic energy and the reception of the return reflection by the vibrating element 100 (as registered by the electrical output of the vibrating element 100).

The processor 102 can be programmed to calculate the distance between the sensor 23 and a target object based on the local speed of sound and the elapsed time between the transmission of the acoustic energy and the reception of the return reflection. The processor 102 can also be programmed to generate an output only when the target object, i.e., the meniscus 19 of the saline solution 18 in the cup 16, is determined to be within the operating distance of the sensor 23.

Specified details of the sensor 23 are presented for exemplary purposes only. Other types of ultrasonic sensors, including ultrasonic sensors in which the generation of the acoustic energy and the reception of the return reflection are performed by separate elements, can be used in the alternative. The term ultrasonic sensor, as used in the specification and claims, is intended to include devices in which the generation of the acoustic energy and the reception of the return reflection are performed by one element, by separate elements disposed in a common housing, and by separate elements not disposed in a common housing.

The sensors 23 are arranged in FIG. 1 on the plate member 27 so that each sensor 23 substantially aligns with the cup 16 of a corresponding one of the packages 12, and the pulses of acoustic energy generated by the sensor 23 are directed toward the cup 16. The pulses of acoustic energy impinge upon the meniscus 19 of the saline solution 18 in the cup 16 if the saline solution 18 is present, thereby generating a return reflection.

As noted above, the processor 102 of each sensor 23 can determine whether the distance between the sensor 23 and the meniscus 19 of the saline solution 18 in the associated cup 16 is within the operating distance of the sensor 23. If the distance between the sensor 23 and the meniscus 19 is within the operating distance of the sensor 23, the processor 102 can generate an output that is transmitted to the PLC 30 by way of the cabling 109 and the connector 111 associated with the sensor 23. The PLC 30 can interpret this output as an indication that saline solution 18 is present in the cup 16 above a predetermined level.

The ability of the sensors 23 to generate an accurate and reliable indication of whether saline solution 18 is present in the cups 16 is dependent upon the spacing between the sensors 23 and the target, i.e., the meniscus 19 of the saline solution 18. The ability of the sensors 23 to detect the saline solution 18 in the cups 16 therefore can be optimized by positioning the sensors 23 at a particular vertical distance from the pallet 21. This distance is denoted by the reference character "D1" in FIG. 2.

The distance D1 can adjusted by varying the vertical position of the plate member 27 on the mounting structure 24, in the above-discussed manner. For example, the vertical position of the plate member 27 can be adjusted so that the distance D1 is approximately 51.00 mm (2.008 inches). Applicants have found that spacing the sensors 23 and the pallet 21 by this distance causes each sensor 23 to generate accurate, repeatable indications that the level of saline solution 18 in the corresponding cup 16 is (or is not) above the approximately half-full level.

The optimal value for the distance D1 is application dependent, and can vary with factors such as the specific sensors used as the sensors 23, the size and spacing of the cups 16, and the ambient environmental conditions. A particular value for the distance D1 is presented for exemplary purposes only.

Each sensor 23 preferably has a beam width of approximately 10 mm (0.39 inch) at the target distance, i.e., at a point approximately 51.00 mm (2.008 inches) from the bottom of the sensor 23. The optimal beam width can vary by application, with factors such as the target distance, the spacing between the sensors 23.

Ultrasonic sensors suitable for use in the present invention can be obtained, for example, from Hyde Park Electronics LLC, of Dayton, Ohio, as the SUPERPROX Model SM300 series ultrasonic sensors. Cabling and connectors suitable for use as the cabling 109 and the connectors 111 can also be obtained, for example, from Hyde Park Electronics LLC, as the AC134 right-angle, 4-conductor, connector/cable assembly.

Each sensor 23 is preferably equipped with a tubular shroud 76. (For clarity, only one of the shrouds 76 is depicted in FIG. 2.) The shroud 76 is secured to the end of the sensor 23 that faces the pallet 21. The shroud 76 can be attached to the sensor 23 by, for example, complementary threads formed on the shroud 76 and the sensor 23.

Figure 5:
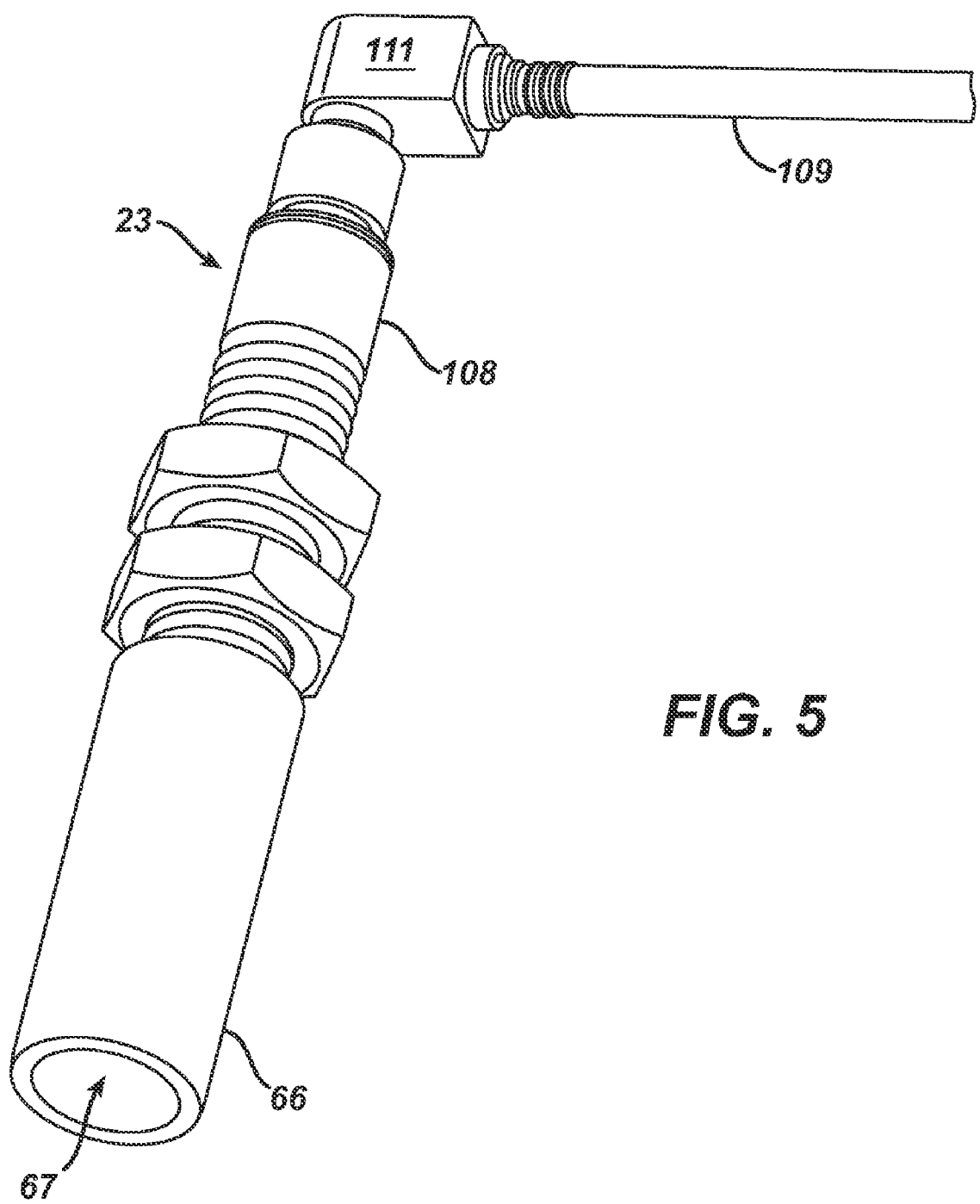
FIG. 5 is a perspective view of an ultrasonic sensor of the system shown in FIGS. 1-4, and a shroud for the ultrasonic sensor.
Figure 6:
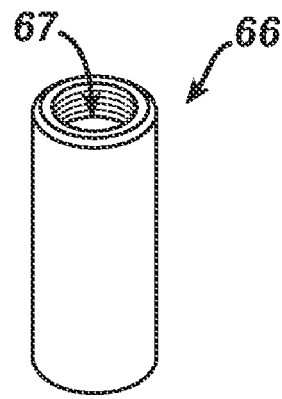
FIG. 6 is a top perspective view of the shroud shown in FIG. 5.
Figure 7:
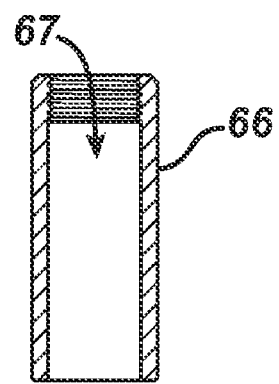
FIG. 7 is a longitudinal cross-sectional view of the shroud shown in FIGS. 5 and 6.

Each shroud 76 permits the pulses of acoustic energy and the return reflections generated by the associated sensor 23 to propagate between the sensor 23 and an associated package 12 on the pallet 21. The shroud 76 also substantially isolates, or shields the pulses and the return reflections from air currents that may be present between the sensor 23 and the package 12. As shown in FIGS. 5-7, each shroud 76 defines an axially-extending passage 77. The passage 77 is in communication with the vibrating element 100 of the sensor 66, so that the pulses of acoustic energy and the return reflections can propagate between the vibrating element 100 and the associated package 12 by way of the passage 77. The passage 77 preferably has a diameter approximately equal to the diameter of a lower end of the sensors 23.

The shrouds 76 can potentially improve the functionality of the sensors 23. In particular, Applicants have found that the functionality of the sensors 23 can be adversely affected by air currents between the sensors 23 and the corresponding packages 21. Air currents that can adversely affect the functionality of the sensors 23 can be generated, for example, by the laminar airflow created inside the enclosure that may house the system 10, or by clean air exhaust that may be generated by secondary equipment such as vacuum generators. The functionality of the sensors 23 can also be adversely affected by the air conditioning or heating systems of the facility in which the system 10 is installed, or by the movement of people or objects in the immediate vicinity of the system 10. It is believed that such air currents can alter the acoustic energy and the return reflections propagating from and to each sensor 23, thereby impeding the ability of the sensor 23 to accurately determine the distance between the sensor 23 and the saline solution 18 in the associated package 21.

Applicants have also found that reducing the sensitivity of the sensors 23 to air currents between the sensors 23 and the packages 12 may require placing the sensors 23 so close to the packages 12 that the functionality of the sensors 23 can be adversely affected. Placing the sensors 23 close enough to the packages 12 to substantially reduce the adverse effects of air currents can make the distance D1 less than that required for the sensors 23 to optimally detect the presence of saline solution 18 in the packages 12.

The shrouds 76 can substantially isolate the pulses of acoustic energy and the return echoes generated by the sensors 23 from air currents between the sensors 23 and the packages 12. The use of the shrouds 76 can thereby allow the sensors 23 to be placed at a sufficient distance D1 from the pallet 21 to facilitate optimal detection of the saline solution 18 in the cups 16 without introducing sensing errors due to air currents between the sensors 23 and the packages 12.

For example, each shroud 76 can be sized so that it extends approximately 33.50 mm (1.319 inch) below the end of the sensor 23. This dimension is denoted by the reference character "D3" in FIG. 2. Sizing the shroud 76 in this manner results in a gap of approximately 24.50 mm (0.9646 inch) between the bottom of the shroud 76 and the top of the pallet 21 when the distance D1 is approximately 51.00 mm. The gap between the bottom of the shroud 76 and the top of the pallet 21 is denoted by the reference character ("D2") in FIG. 2.

The optimal value for the gap D2 is application dependent and can vary with factors such as the specific sensors used as the sensors 23, the magnitude and direction of the air currents between the sensors 23 and the pallet 21, and the ambient environment. A particular value for the gap D2 is presented for exemplary purposes only.

Applicants have also found that the sensors 23 can provide accurate and reliable indications of the levels of saline solution 18 in the cups 16 when bubbles are present in the meniscus 19. Bubbles commonly form in the meniscus 19 as the cups 16 are filled with the saline solution 18. The ability of the sensors 23 to detect the level of the saline solution 18 with bubbles present in the meniscus 19 is believed to represent a substantial advantage in relation to other types of sensors, such as photoelectric sensors, that may experience sensing errors due to the presence of bubbles. Sensing errors can occur in the presence of bubbles because the photoelectric sensor may interpret the top of one or more of the bubbles as the liquid level. Applicants have also found that the sensors 23 are less susceptible than photoelectric sensors to sensing errors caused by misalignment between the sensor and the target.

The foregoing description is provided for the purpose of explanation and is not to be construed as limiting the invention. Although the invention has been described with reference to preferred embodiments or preferred methods, it is understood that the words which have been used herein are words of description and illustration, rather than words of limitation. Furthermore, although the invention has been described herein with reference to particular structure, methods, and embodiments, the invention is not intended to be limited to the particulars disclosed herein, as the invention extends to all structures, methods and uses that are within the scope of the appended claims. Those skilled in the relevant art, having the benefit of the teachings of this specification, may effect numerous modifications to the invention as described herein, and changes may be made without departing from the scope and spirit of the invention as defined by the appended claims. For example, the system 10 can be used to detect fluids other than saline solution, in packages other than packages for contact lenses. Moreover, alternative embodiments of the shrouds 76 can have a shape other than tubular.

What is claimed:

1. A container comprising a surface that forms a cup that holds the saline solution having an ultrasonic sensor that directs acoustic energy at the surface, and detects a return reflection of the acoustic energy; comprising a mounting structure that positions the ultrasonic sensor substantially opposite the surface, wherein the mounting structure comprises a plate member having the ultrasonic sensor mounted thereon, an upper bracket secured to the plate member, a base member, and a lower bracket mounted on the base member and coupled to the upper bracket.

2. The system of claim 1, wherein the lower bracket is coupled to the upper bracket by a fastener that extends through a slot formed in one of the upper and lower brackets.

3. The system of claim 1, wherein the system comprises ten of the ultrasonic sensors mounted on the plate member.

4. The system of claim 3, further comprising a pallet that holds ten of the containers while the ultrasonic sensors direct the acoustic energy at the containers, wherein the ultrasonic sensors are mounted on the plate member so that each of the ultrasonic sensors substantially aligns with a respective one of the containers.

5. A system, comprising:
  a container having a surface that defines a cup, and a fluid disposed in the cup;
  an ultrasonic sensor that directs acoustic energy at the surface, detects a return reflection generated by contact between the acoustic energy and the fluid, and generates an output based on an elapsed time between directing the acoustic energy at the surface of the container and detecting the return reflection; and
  a shroud coupled to the ultrasonic sensor,
wherein the mounting structure comprises a plate member having the ultrasonic sensor mounted thereon, an upper bracket secured to the plate member, a base member, and a lower bracket mounted on the base member and coupled to the upper bracket so that a distance between the ultrasonic sensor and the container can be adjusted.

* * * * *